United States Patent
Al-Shamma'a et al.

(10) Patent No.: US 10,942,136 B2
(45) Date of Patent: Mar. 9, 2021

(54) APPARATUS AND METHOD FOR MEASURING WATER ACTIVITY IN FOOD PRODUCTS

(71) Applicant: Liverpool John Moores University, Liverpool (GB)

(72) Inventors: Ahmed Al-Shamma'a, Liverpool (GB); Alex Mason, Liverpool (GB); Ole Alvseike, Oslo (NO)

(73) Assignee: Liverpool John Moores University, Liverpool (GB)

(*) Notice: Subject to any disclaimer, the term of this patent is extended or adjusted under 35 U.S.C. 154(b) by 341 days.

(21) Appl. No.: 15/756,679

(22) PCT Filed: Aug. 25, 2016

(86) PCT No.: PCT/GB2016/052642
§ 371 (c)(1),
(2) Date: Mar. 1, 2018

(87) PCT Pub. No.: WO2017/037426
PCT Pub. Date: Mar. 9, 2017

(65) Prior Publication Data
US 2018/0252655 A1    Sep. 6, 2018

(30) Foreign Application Priority Data

Sep. 1, 2015 (GB) ...................................... 1515498

(51) Int. Cl.
*G01N 22/04* (2006.01)
*G01N 33/12* (2006.01)

(52) U.S. Cl.
CPC ............. *G01N 22/04* (2013.01); *G01N 33/12* (2013.01)

(58) Field of Classification Search
CPC ............................... G01N 22/04; G01N 33/12
USPC .............................................................. 73/73
See application file for complete search history.

(56) References Cited

U.S. PATENT DOCUMENTS

| | | |
|---|---|---|
| 2006/0043300 A1 | 3/2006 | Campbell et al. |
| 2014/0354299 A1 | 12/2014 | Rapoport |

FOREIGN PATENT DOCUMENTS

| | | |
|---|---|---|
| CN | 102564964 | 7/2012 |
| WO | 2013139912 | 9/2013 |
| WO | WO 2013139912 A1 * | 9/2013 |

OTHER PUBLICATIONS

Translation of Durosset et al, WO 2013139912 A1 (Year: 2013).*
Goh et al., "Investigating Water Holding Capacity (WHC) of Meat Using Microwave Spectroscopy", IEEE (Year: 2012).*
International Preliminary Report on Patentability, dated Mar. 15, 2018, for PCT/GB2016/052642.
Magomed Muradov et al., "Real-time monitoring of meat drying process using microwave spectroscopy"; Sep. 2, 2014; retrieved from the Internet: URL: http://s21s.org/ICST-2014/papers/15699.
(Continued)

*Primary Examiner* — Nathaniel T Woodward
(74) *Attorney, Agent, or Firm* — Hartman Global IP Law; Gary M. Hartman; Domenica N. S. Hartman

(57) ABSTRACT

Apparatus and methods are disclosed using electromagnetic (EM) spectroscopy to obtain non-destructively measurements to determine the water activity ($A_w$) of meat using reflected and/or transmitted signals.

20 Claims, 3 Drawing Sheets

(56) References Cited

OTHER PUBLICATIONS

Goh J H et al. "Investigating water holding capacity (WHC) of meat using microwave spectroscopy"; Sensing Technology (ICST), 2012 Sixth International Conference on, IEEE, Dec. 18, 2012; pp. 243-247, XP032425362; ISBN: 978-1-4673-2246-1; p. 243.
Bjarnadottir S G et al. "Assessing quality parameters in dry-cured ham sing microwave spectroscopy"; Meat Science; vol. 108, Jun. 7, 2015; pp. 109-114, XP029252198; ISSN: 0309-1740.
Great Britain Search and Examination Report dated Jan. 22, 2016.
Great Britain Examination Report dated Aug. 12, 2016.
Great Britain Examination Report dated Jun. 19, 2017.
Great Britain Examination Report dated Nov. 28, 2017.
International Search Report and Written Opinion on PCT/GB2016/052642 dated Nov. 7, 2016.

* cited by examiner

APPARATUS AND METHOD FOR MEASURING WATER ACTIVITY IN FOOD PRODUCTS

TECHNICAL FIELD

The present subject matter relates generally to apparatus and methods for monitoring water activity in food products. More specifically, the apparatus and methods disclosed relate to using electromagnetic spectroscopy to determine water activity in food products.

BACKGROUND

In recent years, the ability to measure food stuff non-destructively and in real-time in the food industry has become increasingly desirable as producers seek to increase productivity and profitability in addition to improving their quality control processes.

There are currently limited options available to food producers for monitoring their products, such as meat, fish, poultry, breads, dairy, etc. Most existing methodologies, used for monitoring food products such as to determine shelf life or to determine when a preserving process is complete, are destructive and/or require a sample to be removed from the food product for testing or require the use of probes which penetrate the food product and lead to issues of damage and decreased product value.

It has been found that the water activity ($A_w$) in a food product can be used to determine the readiness of preserved meat products. In addition, water activity ($A_w$) in a food product can be used to predict the shelf life of food products.

Water activity is defined as the current volume and availability of "free" water in a product available for bacteria and enzymes to operate. Water activity is given in values ranging between 0 (absolute dryness) and 1 (condensed humidity). Meat products have high moisture content, thus their water activity lies in the upper range of the water activity scale for foods.

Fresh meat products have a water activity of approximately 0.95 and above, whilst preserved meat products (preserved using techniques such as cure-drying, freeze-drying etc.) have a lower water activity in a range of approximately 0.7 to 0.92 depending on the specific preserving process used. An exemplary list of typical $A_w$ values for food products can be found at http://onlinelibrary.wiley.com/doi/10.1002/9780470376454.app5/pdf, also provided in Appendix A.

Most bacteria do not grow at water activities below 0.91, and most molds do not grow at water activities below 0.80. Therefore, by measuring water activity, it is possible to predict the shelf life of food products.

A need exists for apparatus and methods for measuring non-destructively the water activity of food products.

SUMMARY

In one embodiment, an apparatus for determining water activity of a food product is provided. The apparatus comprising: a signal generation and acquisition module configured to generate microwave signals; and a sensor configured to radiate the microwave signals at the food product and detect reflection and/or transmission signals from the food product; wherein the signal generation and acquisition module is further configured to measure the detected reflection and/or transmission signals; and wherein a power of 1 Watt or less is generated by the signal generation and acquisition module.

In another embodiment, a power in the range of 1 micro Watt to 1 Watt is generated by the signal generation and acquisition module.

In another embodiment, the apparatus further comprises: a data processing module for determining water activity in the food product based on the measured reflection and/or transmission signals.

In another embodiment, the apparatus further comprises: a data storage module for storing the measured reflection and/or transmission signals.

In another embodiment, the sensor resonates at a frequency greater than 100 MHz.

In another embodiment, the sensor resonates at a frequency in the range of 300 MHz-300 GHz.

In another embodiment, the sensor resonates at a frequency in the range of 2 GHz-6 GHz.

In another embodiment, the sensor resonates at a frequency in the range of 5 GHz-8 GHz.

In another embodiment, the sensor resonates at a frequency in the range of 1 GHz-2 GHz.

In another embodiment, the sensor resonates at a frequency of 3 GHz.

In another embodiment, the sensor is a non-contact sensor.

In another embodiment, the sensor is a non-destructive sensor.

In another embodiment, the signal generation and acquisition module comprises a vector network analyser.

In another embodiment, the microwave signals radiate from 0 to 100 mm from the surface of the sensor.

In another embodiment, the microwave signals radiate from 0 to 10 mm from the surface of the sensor.

In another embodiment, the sensor comprises: a radiating element; a substrate, the radiating element being provided on the substrate; and a feed for coupling the sensor to the signal generation and acquisition module.

In another embodiment, the sensor further comprises: a ground plane provided in contact with the radiating element.

In another embodiment, the radiating element and the ground plane are conductors.

In another embodiment, the substrate comprises an electrical insulator.

In another embodiment, the apparatus further comprises: a disposable cover provided over the sensor whilst measurements are being taken.

In another embodiment, the power generated by the signal generation and acquisition module is fixed for a duration of a measurement cycle.

In another embodiment, the power generated by the signal generation and acquisition module is varied during a measurement cycle.

In one embodiment, a method of determining water activity of a food product is provided. The method comprising: radiating microwave signals from a sensor at the food product; detecting reflection and/or transmission signals from the food product at the sensor; measuring the reflection and/or transmission signals; determining a water activity in the food product as a result of the measured reflection and/or transmission signals; and operating the sensor at a power of 1 watt or less.

In another embodiment, the method further comprises: operating the sensor at a power in the range of 1 micro watt to 1 watt.

In another embodiment, the method further comprises: resonating the sensor at a frequency greater than 100 MHz.

In another embodiment, the method further comprises: resonating the sensor at a frequency in the range of 300 MHz-300 GHz In another embodiment, the method further comprises: resonating the sensor at a frequency in the range of 2 GHz-6 GHz.

In another embodiment, the method further comprises: resonating the sensor at a frequency in the range of 5 GHz-8 GHz.

In another embodiment, the method further comprises: resonating the sensor at a frequency in the range of 1 GHz-2 GHz.

In another embodiment, the method further comprises: resonating the sensor at a frequency at a frequency of 3 GHz.

In another embodiment, the determined water activity in the food product decreases when the measured amplitude of the reflection and/or transmission signals decreases.

In another embodiment, the method further comprises: fixing the operating power of the sensor for a duration of a measurement cycle.

In another embodiment, the method further comprises: varying the operating power of the sensor for a duration of a measurement cycle.

In one embodiment, a method of using an apparatus for determining water activity of a food product is provided. The method comprising: radiating microwave signals from a sensor at the food product; detecting reflection and/or transmission signals from the food product at the sensor; measuring reflection and/or transmission signals at the sensor with a signal generation and acquisition module coupled to the sensor; determining water activity in the food product based on the measured reflection and/or transmission signals; and operating the sensor at a power of 1 watt or less; and wherein the microwave signals resonate at a frequency in the range of 300 MHz-300 GHz.

In another embodiment, the method further comprises: fixing the operating power of the sensor for a duration of a measurement cycle.

In another embodiment, the method further comprises: varying the operating power of the sensor for a duration of a measurement cycle.

The apparatus and methods disclosed enable measurements to be obtained without harming the food product itself. Measurements can be taken at intervals so that the quality and readiness of products can be determined or predicted based on rate of water activity change. Determination of the readiness of products increases productivity as potentially less time in curing rooms is required resulting in reduced energy consumed per preserved product and improved productivity. Determination of shelf life reduces unnecessary wastage of food products.

Additional advantages and novel features will be set forth in part in the description which follows, and in part will become apparent to those skilled in the art upon examination of the following and the accompanying drawings or may be learned by production or operation of the examples. The advantages of the present embodiments may be realized and attained by practice or use of various aspects of the methodologies, instrumentalities and combinations set forth in the detailed examples discussed below.

BRIEF DESCRIPTION OF THE FIGURES

For a better understanding of the embodiments and as to how the same may be carried into effect reference will now be made, by way of example only, to the accompanying figures in which.

In the figures, like reference numerals refer to the same or similar elements.

DETAILED DESCRIPTION

Reference will now be made in detail to the embodiments, examples of which are illustrated in the accompanying figures. In the following detailed description numerous specific details are set forth by way of examples in order to provide a thorough understanding of the relevant teachings. However, it will be apparent to one of ordinary skill in the art that the present teachings may be practiced without these specific details.

A link has been determined between the water activity ($A_w$) of food products and the electromagnetic signature obtained from an electromagnetic sensor provided at the food product. It is suggested that the decreasing amount of water in the sample food product (for example, as a meat is preserved over time, or the food product ages) has an impact on the food products dielectric properties.

In one embodiment, electromagnetic (EM) spectroscopy is used to determine the water activity ($A_w$) of a food product such as meat.

Figure 1:
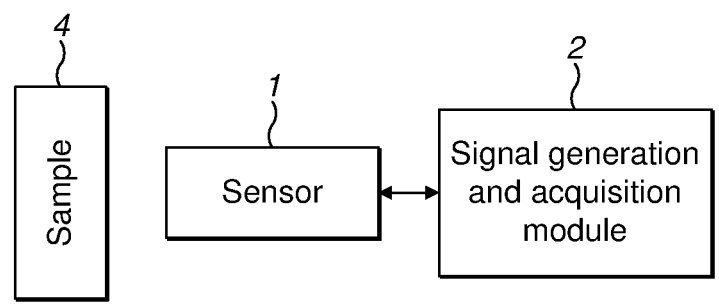
FIG. 1 schematically illustrates apparatus for detecting water activity in a food sample.

FIG. 1 illustrates schematically an apparatus for detecting water activity in a sample food product such as meat. As can be seen from FIG. 1, the apparatus comprises a sensor 1 coupled to a signal generation and acquisition module 2. In another embodiment, the signal generation and acquisition module can be provided as two separate modules, a signal generation module for generating the signal and a signal acquisition module for interpreting the signal. A sample 4, is also illustrated. In one embodiment, the sensor 1 and the signal generation and acquisition module 2 are provided as a single unit. In another embodiment, the sensor 1 and the signal generation and acquisition module 2 are provided as separate units. The signal generation and acquisition module 2 generates the signal to be output by the sensor 1, and interprets changes in the signal detected at the sensor 1.

In one embodiment, the sensor 1 and the signal generation and acquisition module 2 are provided in communication with a data processing module (not illustrated), via wired or wireless communication techniques as known in the art. In another embodiment, the sensor land the signal generation and acquisition module 2 are provided in communication with a data storage module (not illustrated), via wired or wireless communication techniques. In one embodiment, the information stored at the data storage module is analyzed by a data processing module at a later time or date. In another embodiment, information stored at the data storage module is analyzed by a data processing module after a predetermined amount of data has been accumulated. In another embodiment, information stored at data storage module is analyzed by a data processing module in real time. In one embodiment, the data processing module predicts the status of the sample using the water activity readings obtained from the signal generation and acquisition module.

In one embodiment, the signal generation and acquisition module 2 is a Vector Network Analyzer (VNA).

The sensor 1 radiates electromagnetic signals at a predetermined frequency or in a predetermined frequency range at a sample food product and detects the reflected and/or transmitted signals from the sample food product. The signal generation and acquisition module 2 measures the reflected and/or transmitted electromagnetic signals at the sensor 1. A data processing module determines the water activity at the sample product based on the measured reflected and/or transmitted signals. The data processing module may be any known data processing apparatus, such as a computer.

In one embodiment, the sensor 1 comprises a microwave sensor to determine the water activity of the product. In another embodiment, the sensor 1 comprises a radio wave sensor to determine the water activity of the product. In another embodiment, the sensor 1 radiates electromagnetic signals at frequencies greater than 100 MHz to determine the water activity of the product.

Microwaves have wavelengths ranging from 1 mm to 1 m and frequencies between 300 MHz and 300 GHz, whilst radio waves have wavelengths ranging from 1 mm to 100 km and frequencies between 3 kHz and 300 MHz.

The sensor is operated at low power in order to avoid degrading the sample food product. The term "power" when referring to the sensor, is the power generated by the electromagnetic source, which is then transferred to the sensor (the load) via a transmission line. It is not the power of the whole system including the electronics, communications, displays, etc. In one embodiment, a power of 1 Watt or less is generated by the electromagnetic source and transferred to the sensor. In another embodiment, a power in the range of 1 micro Watt to 1 Watt is generated by the electromagnetic source and transferred to the sensor. The power level may be set to a fixed power for the duration of a measurement cycle or may be varied. For example, if the power is varied, it may be gradually increased towards a maximum value during the measurement cycle to assess the food product parameters at various depth profiles, without the sensor physically penetrating the food product.

In one embodiment, the sensor is operated at a number of different frequencies during the measurement cycle in order to obtain an accurate determination of the water activity of the sample food product. The time required to obtain a determination of the water activity depends on the number of discrete frequencies swept (i.e. bandwidth), the greater the number of frequencies required for a measurement, the slower the measurement will be. However, measurements take in the order of milliseconds to <10 s per measurement cycle.

Bandwidth requirements are determined by the complexity of the product. For products with a lot of added materials, such as salts, spices, fats, etc. (for example, a chorizo product) the bandwidth requirements are slower than "simpler" whole animal pieces (for example a ham leg). In addition, the depth of penetration changes on the basis of different products. Changes in the depth of penetration can be achieved through changing the power and/or the frequency at which the sensor operates. Higher frequency and lower power reduces penetration depth.

In addition, it is possible to adjust the depth of penetration/the distance the sensor radiates the signal from the surface of the sensor by changing the sensor size, by changing the operation frequency of the sensor, and/or by changing the geometry of the sensor. Changing the design of the sensor will alter the sensor gain, which in turn impacts the penetration depth. A higher gain results in a larger depth of penetration.

In one embodiment, the sensor is a non-contact sensor and is not required to touch the surface of the food product in order to determine the water activity of the food product. In another embodiment, the sensor is a non-destructive sensor and is only required to gently touch the surface of the food product, without penetrating that surface, in order to determine the water activity of the food product. No damage, loss or contamination is inflicted upon the food product.

In one embodiment, a disposable cover is provided over the sensor whilst measurements are being taken to prevent cross-contamination between food samples. Since the sensor is only required to touch the sample or be placed in close proximity of the sample in order to obtain accurate readings, no damage is inflicted on the sample. When the sensor is required to measure without contact from a short distance, it uses penetrating waves.

In one embodiment, the sensor is provided in close proximity of or in contact with the product surface. Measurements are then taken. In one embodiment, the user initiates measurements, for example by pressing an "on"/"start" button provided at the apparatus. In another embodiment, the apparatus is configured such that providing the sensor in close proximity of/in contact with a food product surface initiates measurements. A single measurement, or a series of measurements are then taken at the chosen location on the sample. This occurs through the generation of a signal by the signal generation and acquisition module, which is transferred to the food product via the sensor, and subsequent acquisition of spectral response from the sensor. The data is processed at a data processing module to determine the water activity of the food product. In one embodiment, the sensor is provided at more than one location at the food product and at least one measurement is taken at each location. In one embodiment, the data processing module is preprogrammed to convert the water activity value into a readiness output to the user, for example a simple "ready" or "not ready" or shelf life value. In another embodiment, a more detailed output of water activity and product historical measurements, showing time dependent trends of the food product change is output. The output can be selected by a user depending on the user's requirements.

In one embodiment, the structure of the sensor is designed such that the sensor resonates an electromagnetic field at approximately 2.4 GHz to give sufficient interaction with the water of the food product, as well as providing a reasonable depth of penetration. In one embodiment, the electromagnetic waves from the sensor penetrate the food product in order to reduce the likelihood of misleading results being obtained due to rapid surface drying.

In one embodiment, the electromagnetic sensor resonates at a frequency greater than 100 MHz. In one embodiment, the electromagnetic sensor resonates at a frequency in the range of 300 MHz-300 GHz. In one embodiment, the electromagnetic sensor resonates at a frequency in the range of 9 kHz-24 GHz. In one embodiment, the electromagnetic sensor resonates at a frequency in the range of 9 kHz-8 GHz. In one embodiment, the electromagnetic sensor resonates at a frequency in the range of 9 kHz-3 GHz. In one embodiment, the electromagnetic sensor resonates at a frequency in the range of 2 GHz-6 GHz. In one embodiment, the electromagnetic sensor resonates at a frequency in the range of 5 GHz-8 GHz. In one embodiment, the electromagnetic sensor resonates at a frequency of approximately 3 GHz. In another embodiment, the electromagnetic sensor resonates at a frequency in the range of 1 GHz-2 GHz.

The apparatus can use either reflected signals (reflection spectra $S_{11}$) or transmitted signals (transmission spectra $S_{21}$), or reflected signals (reflection spectra $S_{11}$) and transmitted signals (transmission spectra $S_{21}$) to determine the water activity of the sample. In one embodiment, the electromagnetic sensor is used for real-time monitoring of food products.

Figure 2:
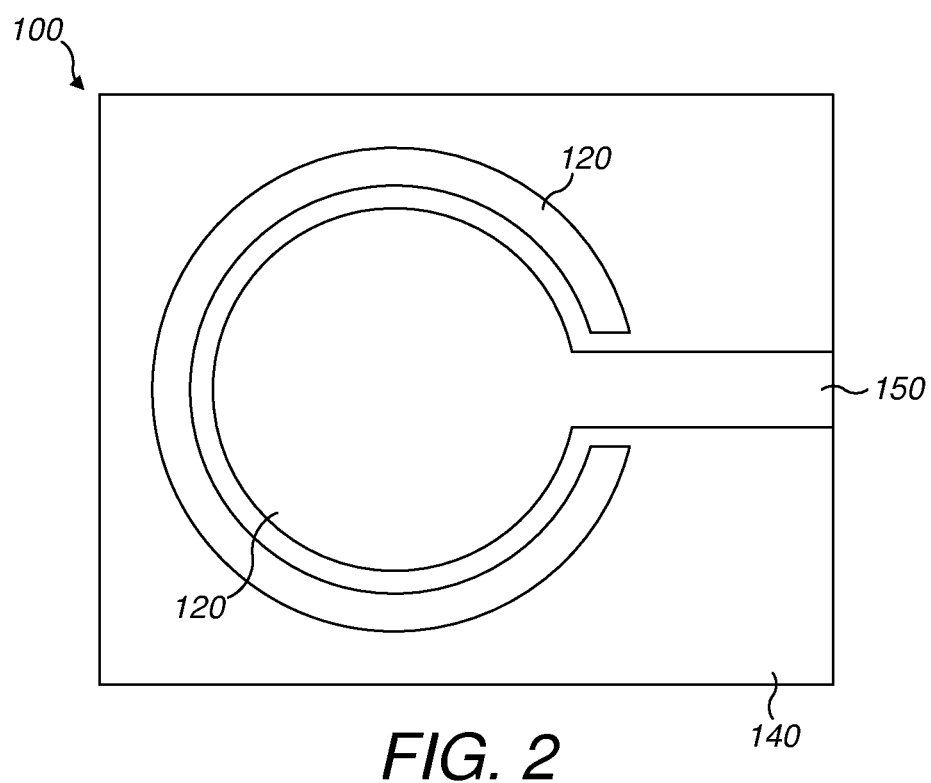
FIG. 2 schematically illustrates one example of a sensor.
Figure 3:
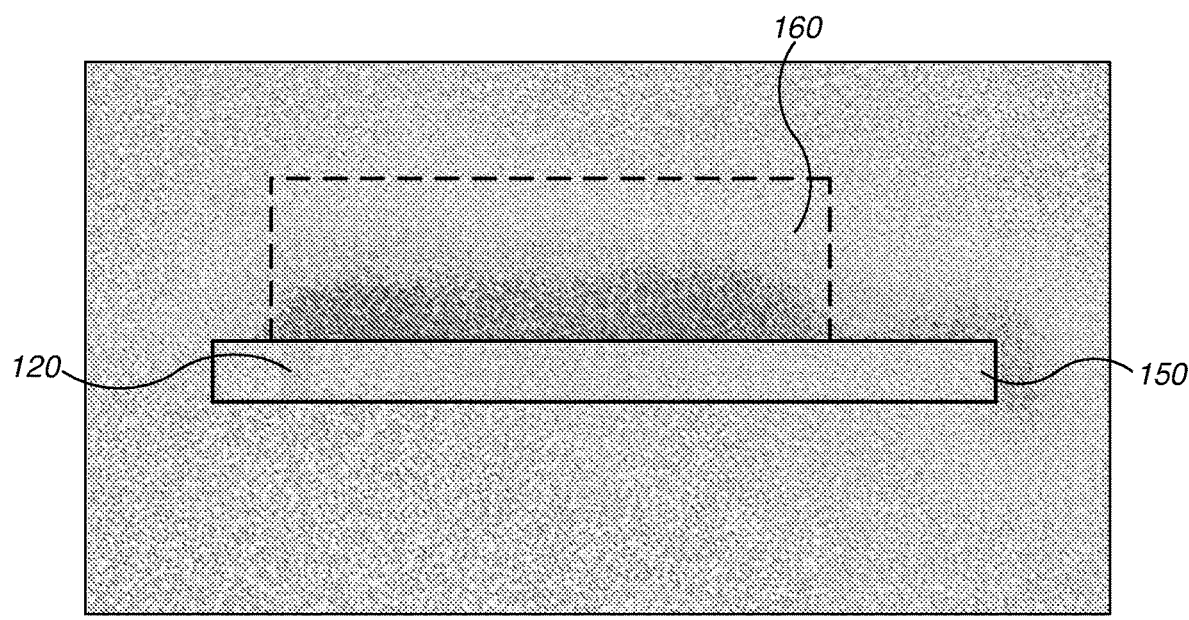
FIG. 3 schematically illustrates the electromagnetic field from the sensor of FIG. 2.

FIG. 2 illustrates schematically one example of a resonant patch (RP) sensor 100 which can be used to determine the water activity of a food product. The sensor 100 comprises an active radiating element 120, a ground plane, a substrate 140 and a feed 150. In one embodiment, the ground plane is not required. The configuration of the resonant patch (RP) sensor illustrated in FIG. 2 is such that the electric field is projected from the sensor surface to enable the determination of water activity in a sample food product. In one embodiment, a resonant patch sensor configured in accordance with FIG. 2 measuring 20 mm long, 20 mm wide and 1.6 mm high has an electric field which projects up to 6 mm from the sensor surface. FIG. 3 illustrates schematically the electric field resonating from the sensor of FIG. 2. As shown in FIG. 3, the sensing area 160 has an electric field projecting up to 6 mm from the sensor surface 120. In one embodiment, the sensor is configured such that the sensing area has an electric field projecting up to 10 mm from the sensor surface.

The depth of penetration required is dependent on the food product. For example, a depth of penetration of a few cm may be desirable for a large ham, and a depth of penetration a few mm for may be desirable a chorizo. In one embodiment, the sensor radiates an electric field from 0 to 100 mm from the surface of the sensor. In another embodiment, the sensor radiates an electric field from 0 to 10 mm from the surface of the sensor.

In one embodiment, the radiating element 120 and the ground plane are conductors. In one embodiment, the substrate material is an electrical insulator. In one embodiment, a conformal polypropylene based spray coating is applied to the sensor to eliminate issues with corrosion.

Figure 4:
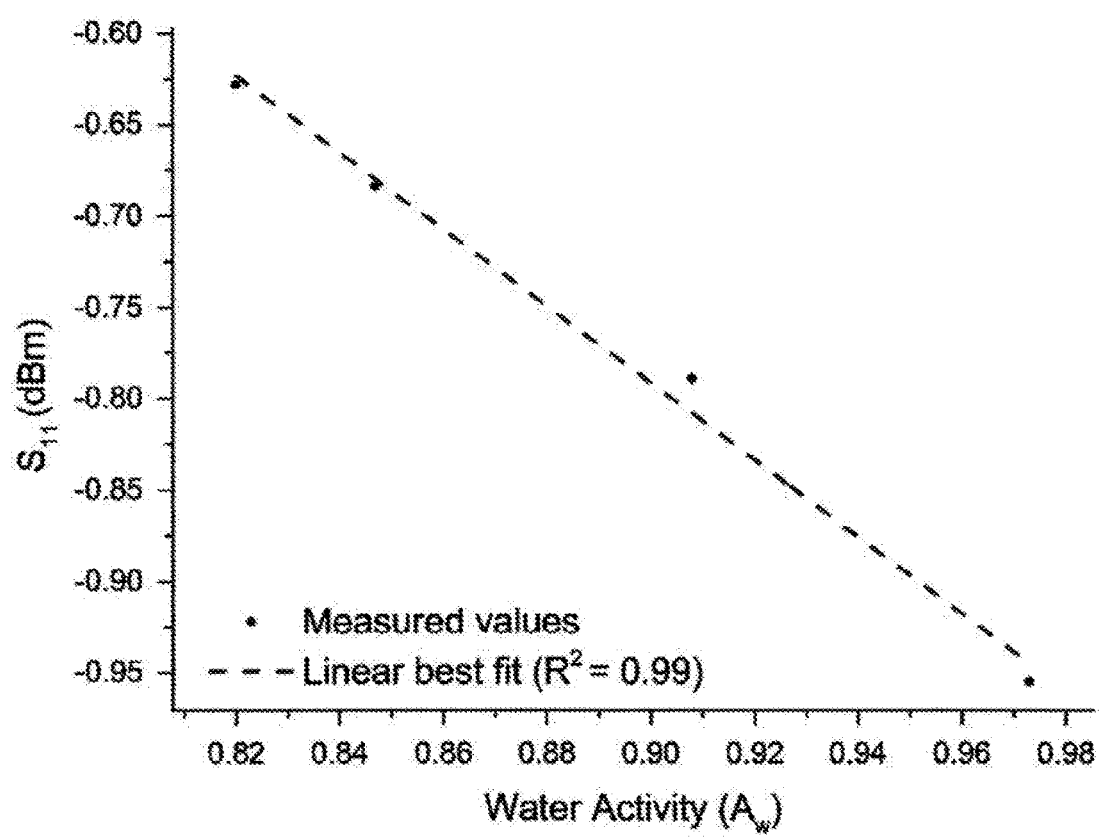
FIG. 4 illustrates $S_{11}$ reflection spectra plotted against water activity.

In one embodiment, a relationship has been determined between water activity ($A_w$) of food products over time and the resulting change in the $S_{11}$ reflection spectra and the $S_{21}$ transmission spectra. The relationship has been determined at a number of different frequencies. FIG. 4 illustrates exemplary $S_{11}$ reflection spectra results obtained plotted against water activity ($A_w$) for continuous measurement of a meat sample.

Figure 5:
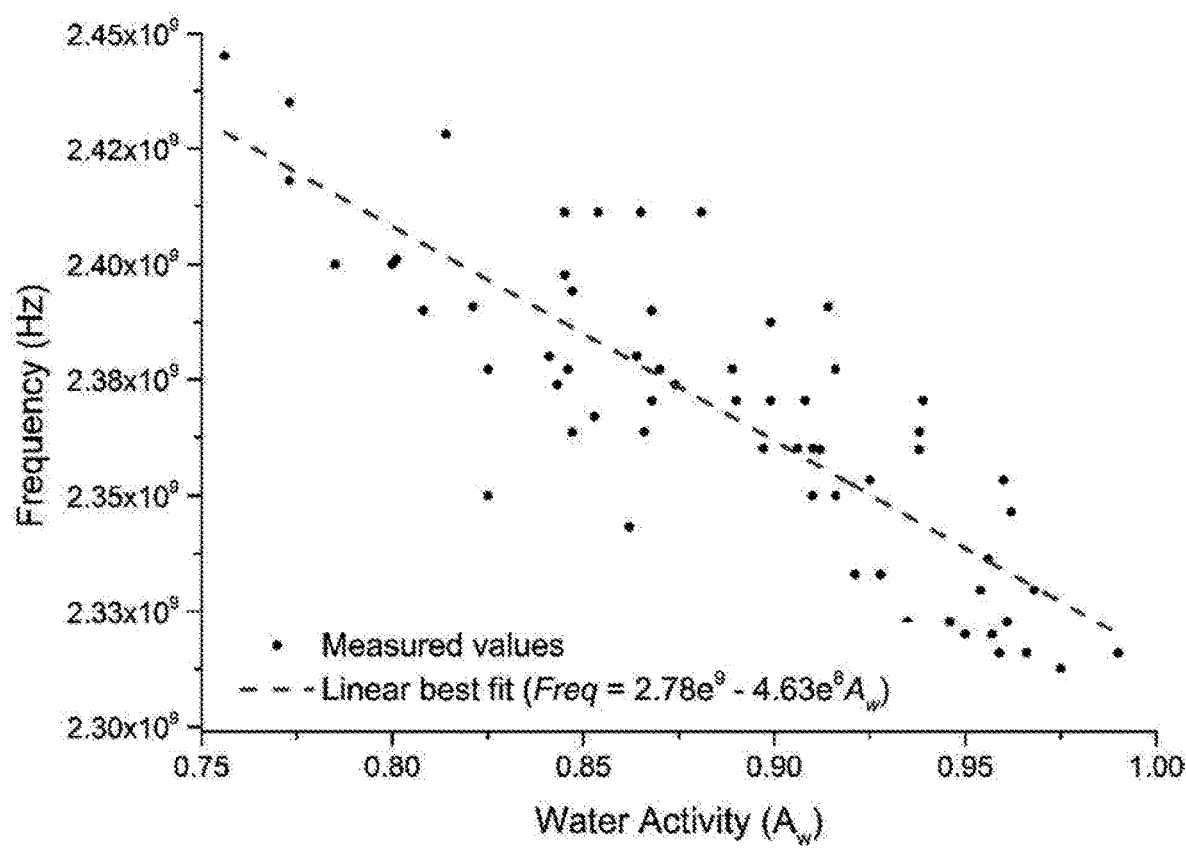
FIG. 5 illustrates discrete $S_{11}$ measurements plotted against water activity.

FIG. 5 illustrates one example of discrete $S_{11}$ measurements plotted against water activity for a meat sample, obtained using an exemplary sensor at 2.3-2.4 GHz frequency, and with a sample meat product. The samples used in this work were derived from pork loin which had been cut into approximately 100×100 mm samples, and of approximately 25 mm thickness. The meat was salted as per a standard method, and stored for 2 weeks at 5° C. to allow equalization. The samples were then left to cure at approximately 14° C., with measurements being taken twice daily with the described electromagnetic sensor apparatus. The industry standard measurement for water activity was also taken using an AquaLab Water Activity meter. The AquaLab Water Activity meter test is destructive and takes up to 20 minutes per sample. The electromagnetic sensor described herein, by comparison, achieves a measurement within seconds and is non-destructive. The sensor exhibits a frequency shift which can be correlated with the water activity. FIG. 5 illustrates the water activity measurements in the range of 1 to 0.75, however, the sensor is also capable of obtaining lower values of water activity.

FIG. 5 also includes a formula determined for the sample food product of FIG. 5. The formulae can be used to calculate the water activity of the sample food product when a reflected frequency is detected in Hz. In FIG. 5, the following formulae is provided:

$$\text{Frequency} = 2.78 \times 10^9 - 4.63 \times 10^8 A_w \qquad \text{Equation 1.}$$

In order to calculate the water activity of the sample food product from the detected reflection frequency, equation 1 can be rewritten as:

$$A_w = (2.78 \times 10^9 - \text{Frequency}) \div 4.63 \times 10^8 \qquad \text{Equation 2.}$$

The water activity value can then be used to determine whether the food product has been preserved and/or to determine the shelf life of the product.

In one embodiment, the electromagnetic sensor uses a reflection frequency in the range of 4.63-4.65 GHz and a transmission frequency in the range of 4.85-4.87 GHz. These frequencies give high correlation for both high and low salt food products.

FIG. 4 illustrates that with decreasing amplitude on the $S_{11}$ spectra's, the water activity in the food product (in this example a meat sample) increases. FIG. 5 illustrates that with decreasing frequency on the $S_{11}$ spectra's, the water activity in the food product (in this example a meat sample) increases. This applies for both high and low salt food products.

In one embodiment, it is possible to predict a meat samples status, to establish whether the sample has been preserved or whether the sample requires further preserving, based on the determined water activity levels identified by using microwave spectroscopy for either or both $S_{11}$ and $S_{21}$ spectra. Significant savings in time and energy can be made through knowing at which stage a product is at in the preserving process. Given that preserving processes take place over days, weeks or even months, knowing whether a product is ready earlier than expected allows it to be shipped for sale and the precious temperature and humidity controlled environments can be utilised effectively for new products.

In one embodiment, it is possible to predict a shelf-life for a food product, based on the determined water activity levels identified by using microwave spectroscopy for either or both $S_{11}$ and $S_{21}$ spectra. As stated above, water activity is the measurement of the amount of free water available in a product for bacteria to grow, the growth of certain bacteria leading to spoilage of the food product. Thus, low water activity tends to lead to a longer shelf life (as with cured meats), and high water activity tends to lead to a shorter shelf life. By measuring the water activity of a food product, it is possible to predict the shelf life of that food product more accurately than current practice which errs on side of "safety", leading to waste. Current practices result in food products being removed from shelves prior to spoilage simply because the "best before date" has been passed. In addition, current practices apply the same shelf life to groups of products, whereas it will be possible to determine the shelf life more accurately of individual products if desired using the apparatus described.

Those skilled in the art will appreciate that while the foregoing has described what is considered to be the best mode and where appropriate other modes of performing the invention, the invention should not be limited to the specific configurations and methods disclosed in this description of the preferred embodiment. Those skilled in the art will recognize that the invention has a broad range of applications, and that the embodiments may take a wide range of modifications without departing from the inventive concept as defined in the appended claims.

The invention claimed is:

1. An apparatus for determining water activity of a food product, the apparatus comprising:
   a signal generation and acquisition module configured to generate microwave signals; and
   a sensor configured to radiate the microwave signals at the food product and detect reflection and/or transmission signals from the food product;
   wherein the signal generation and acquisition module is further configured to measure the detected reflection and/or transmission signals; and
   wherein a power of 1 Watt or less is generated by the signal generation and acquisition module.

2. The apparatus of claim 1, wherein a power in the range of 1 micro Watt to 1 Watt is generated by the signal generation and acquisition module.

3. The apparatus of claim 1, further comprising:
   a data processing module for determining water activity in the food product based on the measured reflection and/or transmission signals.

4. The apparatus of claim 1, wherein the sensor resonates at a frequency greater than 100 MHZ.

5. The apparatus of claim 1, wherein the sensor resonates at a frequency in the range of 300 MHz-300 GHz.

6. The apparatus of claim 1, wherein the sensor is a non-contact sensor.

7. The apparatus of claim 1, wherein the sensor is a non-destructive sensor.

8. The apparatus of claim 1, wherein the microwave signals radiate from 0 to 100 mm from the surface of the sensor.

9. The apparatus of claim 1, wherein the sensor comprises:
   a radiating element;
   a substrate, the radiating element being provided on the substrate; and
   a feed for coupling the sensor to the signal generation and acquisition module.

10. The apparatus of claim 9, wherein the sensor further comprises:
    a ground plane provided in contact with the radiating element.

11. The apparatus of claim 9, wherein the radiating element and the ground plane are conductors.

12. The apparatus of claim 1, wherein the power generated by the signal generation and acquisition module is fixed for a duration of a measurement cycle.

13. The apparatus of claim 1, wherein the power generated by the signal generation and acquisition module is varied during a measurement cycle.

14. A method of determining water activity of a food product, the method comprising:
    radiating microwave signals from a sensor at the food product;
    detecting reflection and/or transmission signals from the food product at the sensor;
    measuring the reflection and/or transmission signals;
    determining a water activity in the food product as a result of the measured reflection and/or transmission signals; and
    operating the sensor at a power of 1 watt or less.

15. The method of claim 14, further comprising:
    operating the sensor at a power in the range of 1 micro watt to 1 watt.

16. The method of claim 14, further comprising:
    resonating the sensor at a frequency greater than 100 MHZ.

17. The method of claim 14, further comprising:
    resonating the sensor at a frequency in the range of 300 MHz-300 GHz.

18. The method of claim 14, wherein the determined water activity in the food product decreases when the measured amplitude of the reflection and/or transmission signals decreases.

19. The method of claim 14, further comprising:
    fixing the operating power of the sensor for a duration of a measurement cycle.

20. The method of claim 14, further comprising:
    varying the operating power of the sensor for a duration of a measurement cycle.

* * * * *